(12) United States Patent
Beden

(10) Patent No.: US 10,794,791 B2
(45) Date of Patent: Oct. 6, 2020

(54) METHOD FOR CHECKING A CONNECTION STATE BETWEEN A BLOOD TREATMENT APPARATUS AND A BLOOD TUBING SET, AND APPARATUSES

(71) Applicant: Fresenius Medical Care Deutschland GmbH, Bad Homburg (DE)

(72) Inventor: Josef Beden, Mainz-Kastel (DE)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 275 days.

(21) Appl. No.: 15/549,282

(22) PCT Filed: Feb. 12, 2016

(86) PCT No.: PCT/EP2016/053032
§ 371 (c)(1),
(2) Date: Aug. 7, 2017

(87) PCT Pub. No.: WO2016/128555
PCT Pub. Date: Aug. 18, 2016

(65) Prior Publication Data
US 2018/0024022 A1     Jan. 25, 2018

(30) Foreign Application Priority Data
Feb. 12, 2015 (DE) .................. 10 2015 102 040

(51) Int. Cl.
*G01M 3/02* (2006.01)
*A61M 1/36* (2006.01)
*A61M 39/10* (2006.01)

(52) U.S. Cl.
CPC ............. *G01M 3/02* (2013.01); *A61M 1/367* (2013.01); *A61M 1/3627* (2013.01);
(Continued)

(58) Field of Classification Search
CPC ...... G01M 3/02; A61M 1/3627; A61M 1/367; A61M 2039/1005; A61M 2039/1044; A61M 2205/14
(Continued)

(56) References Cited

U.S. PATENT DOCUMENTS

| 2009/0152179 A1 | 6/2009 | Kopperschmidt |
| 2012/0083726 A1 | 5/2012 | Kopperschmidt et al. |

(Continued)

FOREIGN PATENT DOCUMENTS

| DE | 3442744 | 6/1986 |
| DE | 102011108784 | 1/2013 |

(Continued)

OTHER PUBLICATIONS

English translation of International Search Report for International Application No. PCT/EP2016/053032, dated Apr. 25, 2016, 6 pages.
(Continued)

*Primary Examiner* — Tarun Sinha
(74) *Attorney, Agent, or Firm* — Fish & Richardson P.C.

(57) ABSTRACT

The disclosure relates to a method for checking a connection between a compressed air outlet of a blood treatment apparatus and a pressure measuring line of an extracorporeal blood tubing set. The methods disclosed include providing a blood treatment apparatus having a compressed air line. A compressed air device is in fluid communication with the compressed air line for generating pressure within the compressed air line. A compressed air outlet is in fluid communication with both the compressed air line and an exterior of the blood treatment apparatus. The compressed air outlet is connectable with a pressure measuring line and a pressure sensor. The method also includes building up a pressure and an air flow in the compressed air line and/or at the compressed air outlet, measuring a pressure at the compressed
(Continued)

air outlet or in the compressed air line, and evaluating an increase of the measured pressure.

21 Claims, 4 Drawing Sheets

(52) U.S. Cl.
CPC .............. *A61M 2039/1005* (2013.01); *A61M 2039/1044* (2013.01); *A61M 2205/14* (2013.01); *A61M 2205/276* (2013.01); *A61M 2205/3331* (2013.01); *A61M 2205/50* (2013.01); *A61M 2205/70* (2013.01); *A61M 2205/7536* (2013.01)

(58) Field of Classification Search
USPC ...................................... 73/40.5 R See application file for complete search history.

(56) References Cited

U.S. PATENT DOCUMENTS

| | | |
|---|---|---|
| 2013/0028788 A1 | 1/2013 | Gronau et al. |
| 2015/0335809 A1* | 11/2015 | Stuva ...................... A61M 1/14 |
| | | 137/15.01 |
| 2018/0024022 A1 | 1/2018 | Beden |

FOREIGN PATENT DOCUMENTS

| | | |
|---|---|---|
| JP | H02-289259 | 11/1990 |
| JP | 2002-095741 | 4/2002 |
| JP | 2007-282928 | 11/2007 |
| WO | 2013017236 | 2/2013 |
| WO | WO 2014/099779 | 6/2014 |

OTHER PUBLICATIONS

International Preliminary Report on Patentability in Application No. PCT/EP2016/053032, dated Aug. 15, 2017, 8 pages.

* cited by examiner

METHOD FOR CHECKING A CONNECTION STATE BETWEEN A BLOOD TREATMENT APPARATUS AND A BLOOD TUBING SET, AND APPARATUSES

CROSS-REFERENCE TO RELATED APPLICATIONS

The present application is the national stage entry of International Patent Application No. PCT/EP2016/053032, filed on Feb. 12, 2016, and claims priority to Application No. DE 10 2015 102 040.8, filed in the Federal Republic of Germany on Feb. 12, 2015, the disclosures of which are expressly incorporated herein in entirety by reference thereto.

TECHNICAL FIELD

The disclosure relates to a method, a detection device, a medical blood treatment apparatus, and a blood tubing set for providing blood treatment to a patient. Furthermore, the disclosure relates to a digital storage medium, a computer program product, and a computer program for controlling a blood treatment apparatus providing blood treatment to a patient.

BACKGROUND

Machine-induced or automatic tests for checking the function and reliability of medical functional devices, such as extracorporeal blood tubes, blood cassettes and the like, or their correct connection state with the blood treatment apparatus are known from WO 2013/017236 A1. Such a test may for example be a pressure-holding test. The test is executed after the respective functional device is connected with the blood treatment apparatus, i.e. after the blood treatment apparatus has been equipped with the functional device, and prior to beginning with the treatment of the patient.

SUMMARY

Certain aspects of this disclosure include a method for checking the connection state between a blood tubing set and the blood treatment apparatus. In addition, suitable apparatuses, a suitable digital storage medium, a suitable computer program product, and a suitable computer program are disclosed herein.

A method is proposed for checking a connection between a compressed air outlet of a blood treatment apparatus and a pressure measuring line of an extracorporeal blood tubing set.

The method encompasses providing a blood treatment apparatus. The blood treatment apparatus comprises a compressed air line and a compressed air device being in fluid communication with the compressed air line, wherein the compressed air device serves for generating pressure and air flow within the compressed air line.

The blood treatment apparatus comprises a compressed air outlet in fluid communication with both the compressed air line and an exterior of the blood treatment apparatus.

The compressed air outlet is embodied to be connectable to a pressure measuring line. Here, it is exemplarily embodied as or comprises a connection element such as a port, a connector, a Luer connector (or male or female part of a Luer connector) or the like.

The blood treatment apparatus further comprises a pressure sensor arranged for measuring pressure prevailing at the compressed air outlet or in the compressed air line.

The method further encompasses a building up of pressure, preferably air pressure, and flow of air in the compressed air line and/or at the compressed air outlet. The pressure and the flow of air are generated by the compressed air device.

The method further encompasses measuring pressure at the compressed air outlet or in the pressure line, for example as an absolute value or as a pressure change over time. This is measured, respectively, with the pressure sensor.

Finally, the method encompasses an evaluation of an increase of the measured pressure, for example with respect to an initial value, or of an increase of the pressure over time. The evaluation is preferably done, respectively, by comparing the measured pressure or a measured pressure increase with previously measured or stored or saved values, thresholds, ranges or courses.

The detection device is programmed and/or configured to execute the method, in particular after having provided the blood treatment apparatus and in interaction with the latter.

The blood treatment apparatus comprises at least one detection device and/or is connected therewith in signal transmission or it is in a signal-transmitting relationship thereto.

The blood tubing set is thus used in a blood treatment carried out by a blood treatment apparatus, in particular in a method described herein. The blood tubing set comprises at least a pressure measuring line, a connector for connecting the pressure measuring line to the blood treatment apparatus and at least an air-permeable membrane arranged in the pressure measuring line or in the connector. An air-permeable membrane allows a flow of air or of gas through the membrane.

A digital, in particular a non-volatile storage medium, more specifically a machine-readable medium, for example a disk, CD, DVD or EPROM, with electrically readable control signals, may interact with a programmable computer system such that the machine-induced or machinery steps of a method described herein are prompted.

The computer program product comprises a program code that is volatile or saved on a machine-readable medium or a signal wave for prompting the machine-induced steps of the method, when the computer program product runs on a computer. A computer program product can be understood as, for example, a computer program which is stored or saved on a medium, an embedded system as a comprehensive system with a computer program (e.g. an electronic device with a computer program), a network of computer-implemented computer programs (e.g. a client-server system, a cloud computing system, etc.), or a computer on which a computer product is loaded, executed, saved or developed.

The term machine-readable medium as used herein denotes in certain embodiments, a medium containing data or information which is interpretable by software and/or hardware. The medium may be a data medium, like a disk, a CD, a DVD, an USB stick, a flashcard, an SD card or the like.

A computer program comprises a program code for prompting the machine-induced steps of the method described herein when the computer program runs on a computer. A computer program can be understood as, for example, a physical, ready-for-distribution software product which comprises a computer program.

It applies for the digital storage medium, for the computer program product and for the computer program that all, specific or some of the machine-induced steps are prompted. This applies particularly in interaction with a detection device and/or a provided blood treatment apparatus as described herein.

In all of the previous and following embodiments, the use of the expression "may be" or "may have" and so on, is to be understood synonymously with "preferably is" or "preferably has," respectively, and so on, and is intended to illustrate an embodiment.

Whenever a numerical value is mentioned herein, the person skilled in the art understands it as an indication of a numerical lower limit. Unless it leads the person skilled in the art to an evident contradiction, the skilled person implicitly understands when specifying for example "one" always as "at least one". This understanding is also evenhandedly encompassed as the interpretation that a numeric word, for example, "one" may alternatively mean "exactly one", wherever this is not evidently technically impossible for the skilled person. Both are encompassed and apply herein to all used numerical values.

Further advantageous developments of the present invention are each subject matter of the dependent claims.

Embodiments may comprise some or all of the following features.

In some particular exemplary embodiments, the evaluation is a comparison with a known pressure value or an initial pressure value, or is calculating a difference (e.g. with respect to a known or previously measured initial pressure or a control value, e.g. pressure of 0 mmHg). Thereby, an absolute, a relative or a percentage increase may be detected or gained.

In certain exemplary embodiments, a maximum pressure threshold is preset. This exceeds a threshold which the measured pressure must reach in order to indicate the assessment that a connection exists. Providing the maximum pressure threshold makes it optionally possible to assert or detect a complete closure or locking of the compressed air line of the blood treatment apparatus. Such a complete closure may advantageously allow assuming for example a defect, device-sided air-permeable membrane (e.g., see below, or e.g. hydrophobic filter) or be a result thereof.

In some exemplary embodiments, the evaluation of an increase is not an, or encompasses no, evaluation of a drop of pressure, e.g. no evaluation of a drop of the measured pressure with respect to an initial value or to a pressure value measured intermediately.

In certain exemplary embodiments, the pressure sensor is part of a return pressure measuring unit with which also the venous blood pressure in the blood tubing system may be measured.

In some exemplary embodiments, the air-permeable membrane is or comprises a transducer protector membrane (abbreviated: TP).

In certain exemplary embodiments, the pressure measuring line comprises a connector, preferably a Luer connector which is connectable to the compressed air outlet of the blood treatment apparatus.

In certain exemplary embodiments, the air-permeable membrane is arranged in the connector, if any.

The pressure value measured with the pressure sensor and evaluated may be in particular the maximum or the highest pressure value measured. More so, it may be the highest pressure value measured until the method is stopped due to a time-out, if a time-out occurs. The corresponding, preset maximum time which the time-out should not or must not exceed, may be e.g. up to 3, 5, 7, 10 s (seconds). It is preferred however to limit a time-out to 1 to 2 s, in particular to a maximum of 1 s. This short period of time allows multiple repetitions of the method described herein, in particular before the blood tubing set is connected and thus no longer considered as sterile.

In some exemplary embodiments, the evaluation of the increase of the measured pressure or its increase over time is or encompasses an indication of the assessment regarding the connection between the compressed air outlet and the pressure measuring line on the basis of the evaluation of the increase.

This indication or statement may optionally be quantative or qualitative. It may for example state or indicate "correct", "correctly connected", "not connected" and/or "connected but not correctly".

In some exemplary embodiments, the indication regarding the connection states that a connection between the compressed air outlet and the pressure measuring line exists or does not exist, and/or that it is incorrect or correct.

In some particular exemplary embodiments, a "connection" may be understood as a state of connection. It may be a mechanical connection between two or more connection elements.

In some particular exemplary embodiments, the method encompasses providing a complete or closed collection (e.g. as a list, as a file, as part of a database or the like) of minimum values, maximum values, patterns, characteristic curves, pressure flow characteristic curve, pressure flow velocity characteristic curve and/or courses of pressures or pressure increases over time, which have been collected for or which designate, preferably uniquely or unambiguously, two or more preselected, different or distinct from each other, pressure measuring lines or designs, types or models.

In these embodiments, the evaluation of the increase of the measured pressure or of its course over time encompasses or consists of checking whether the increase of the course (or a pattern, a characteristic curve or a course thereof) is included in the complete list. The result of this evaluation may optionally be output.

In some particular exemplary embodiments, building up pressure by the compressed air device is carried out repeatedly, (or the pressure is repeatedly built up) e.g. in preselected time intervals.

In some particular exemplary embodiments, building up pressure by the compressed air device is continuous, i.e. from the beginning of the method until its termination. Thus, the compressed air device continuously provides or supplies in these embodiments excess pressure building up pressure consequently. It provides a constant positive (i.e. greater than zero) volume flow.

The method is terminated or interrupted if, for example, the method states that a correct connection exists, which has been detected from the fact that the measured pressure has risen to or above a preselected threshold.

The method is terminated, for example, if the method does not allow to indicate an assessment within a preselected period of time that a correct connection exists. The latter may be detected from the fact that the measured pressure has not risen to or has not exceeded a preselected threshold until the end of the preselected period of time.

In specific exemplary embodiments, the threshold, which the measured pressure must reach in order to pass the test method is preselected with regard to the used blood tubing set or the used pressure measuring line. Pre-selecting may be a step or part of the method. It may further be optionally automated, e.g. in that the blood treatment apparatus inquires the kind (type, model) of the blood tubing set or of the pressure measuring line used.

In some exemplary embodiments, no reduced pressure or negative pressure or vacuum is applied at the compressed air outlet and/or in the pressure measuring line.

In some particular exemplary embodiments, the indication of an assessment regarding the connection is or reveals that a connection exists or does not exist, if a preselected minimum pressure increase, a preselected minimum pressure or a preselected course of the pressure increase over time is not reached or not detected.

In certain exemplary embodiments, no pressure-holding test is carried out.

In some particular exemplary embodiments, the blood tubing set in the pressure measuring line has no pressure dome.

In specific exemplary embodiments, the blood tubing set has no air-permeable diaphragm known, for example, from a pressure dome in the pressure measuring line.

In some exemplary embodiments, the blood tubing set encompasses or encloses no closed volume in the pressure measuring line. Preferably the pressure measuring line is in these embodiments rather open at an end (which is not connected to the compressed air outlet) or extends or opens in a sufficiently large volume as that of the bubble trap or of the venous blood chamber. One may speak here of an "open line".

In some particular exemplary embodiments, the pressure measuring line is open to a venous or arterial patient line or to another line of the blood tubing set.

In some exemplary embodiment, the indication of the assessment is or reveals that a connection does not exist or does not correctly exist, if the measured pressure increase does not reach a preselected pressure value or does not exceed or remains below the preselected pressure value.

In some particular exemplary embodiments, the indication of the assessment is or reveals that the connection does not exist or does not correctly exist, if the measured pressure does not reach or does not exceed a preselected pressure value (P-V) within a preselected period of time, which for example starts with the application of pressure and air flow by the compressed air device, (herein also denoted as time-out).

In some particular embodiments, when the indication of the assessment reveals that the connection does not exist or does not correctly exist, an error message (e.g. optical and/or acoustic) is issued or triggered and/or the method is terminated or interrupted.

In some particular embodiments, the method of any embodiment is repeated if the indication of the assessment regarding the connection is or reveals that the connection does not exist or does not correctly exist or if the user requests this (such as by actuating an actuation or control element like a switch, a touch-screen surface or the like).

In some particular embodiments, the method encompasses disabling the beginning of a blood treatment by the provided blood treatment apparatus, or, in case the treatment has already begun, terminating or interrupting an ongoing blood treatment. This may apply in particular for a blood treatment in which the extracorporeal blood tubing set is used or supposed to be used as intended. Disabling, terminating, or interrupting is carried out in these embodiments if the indication of the assessment regarding the connection reveals that the connection does not exist, does not correctly exist, it has not correctly occurred, or that the increase of the pressure or its course is not included in the completed list.

In some particular embodiments, the method encompasses blocking or disabling some or all the treatment modalities of the provided blood treatment apparatus and/or restricting treatment parameters of the blood treatment method executable or performable by the provided blood treatment apparatus. Blocking is carried out in these embodiments if the indication of the assessment regarding the connection reveals that the connection does not exist, does not correctly exist, has not correctly occurred, or that the increase of the pressure or its course is not included in the completed list.

In some particular exemplary embodiments, the method begins and/or ends prior to beginning a treatment of a patient with the extracorporeal blood tubing set.

In some particular exemplary embodiments, the blood treatment apparatus or the provided blood treatment apparatus is an apparatus for apheresis or dialysis, in particular for hemodialysis, hemofiltration or hemodiafiltration.

In some particular exemplary embodiments, the detection device comprises at least one display unit, or is connected thereto in signal transmission, for displaying a result of the execution of the method. The display unit may be a display, an error display or the like.

In some particular exemplary embodiments, the detection device comprises at least one alarm means configured or programmed to issue an alarm when the result of executing the method reveals that the connection does not exist or does not correctly exist. The detection device is alternatively in signal transmission with such an alarm device.

In some particular exemplary embodiments, the detection device is programmed and/or configured to interfere with the provided blood treatment apparatus, in case the result of executing the method reveals that the connection does not exist or does not correctly exist, or that the increase of the course is not included in the complete list, such that at least one treatment option, for which the blood treatment apparatus is designed, is temporarily not performable or feasible, and/or that the treatment is temporarily not performable by the blood treatment apparatus with preselected treatment parameters.

In some particular exemplary embodiments, the detection device is a control device and/or a function test monitor, or it comprises the like, respectively.

In some particular exemplary embodiments, the blood treatment apparatus comprises an air-permeable membrane in the compressed air line.

Measuring a pressure or a pressure change may encompass any kind or way of determining, for example, measuring with pressure sensor, however also a calculation or a conclusion based on pressure values provided by the pressure sensor.

In some exemplary embodiments, the herein described devices, apparatuses or other objects comprise, or are connected to, devices, apparatuses or other objects required for executing the herein described method steps or test steps, which are preferably named after the respective step.

The detection device comprises in certain exemplary embodiments at least one alarm device for triggering an alarm. The alarm device may be provided or configured for triggering an alarm in case the indication of an assessment reveals that there is no, or no correct, connection. The alarm may be acoustic and/or visual.

Some or all of the embodiments may provide for or exhibit one or several of the previous or following advantages.

An increased safety of the patient may be achieved as safety-relevant functions of the used blood tubing set, namely connecting it to measure pressure, and the blood treatment apparatus are controlled or checked.

Since the method may be carried out while preparing or equipping the blood treatment apparatus, a technical failure may be detected before the patient is connected and before blood has come in contact with the blood treatment apparatus and with the extracorporeal blood circuit or with the blood tubing set. This prevents an unnecessary wastage of single-use items. It further enables, in case of failure, an easy and early exchange or replacement of defect pressure measuring lines or blood tubing sets.

Since the method may in some particular embodiments be carried out without any involvement from the staff in charge and may run automatically, it is advantageously possible to detect errors or failures while saving time and already prior to the begin of the treatment. Since the procedure described herein is performable in an automated manner, it additionally ensures that relevant test steps or procedures cannot be forgotten.

Some embodiments shall be exemplarily explained in the following by way of the accompanying drawings, in which identical reference numerals designate same or similar elements. In the partially simplified figures,

DETAILED DESCRIPTION

Figure 1:
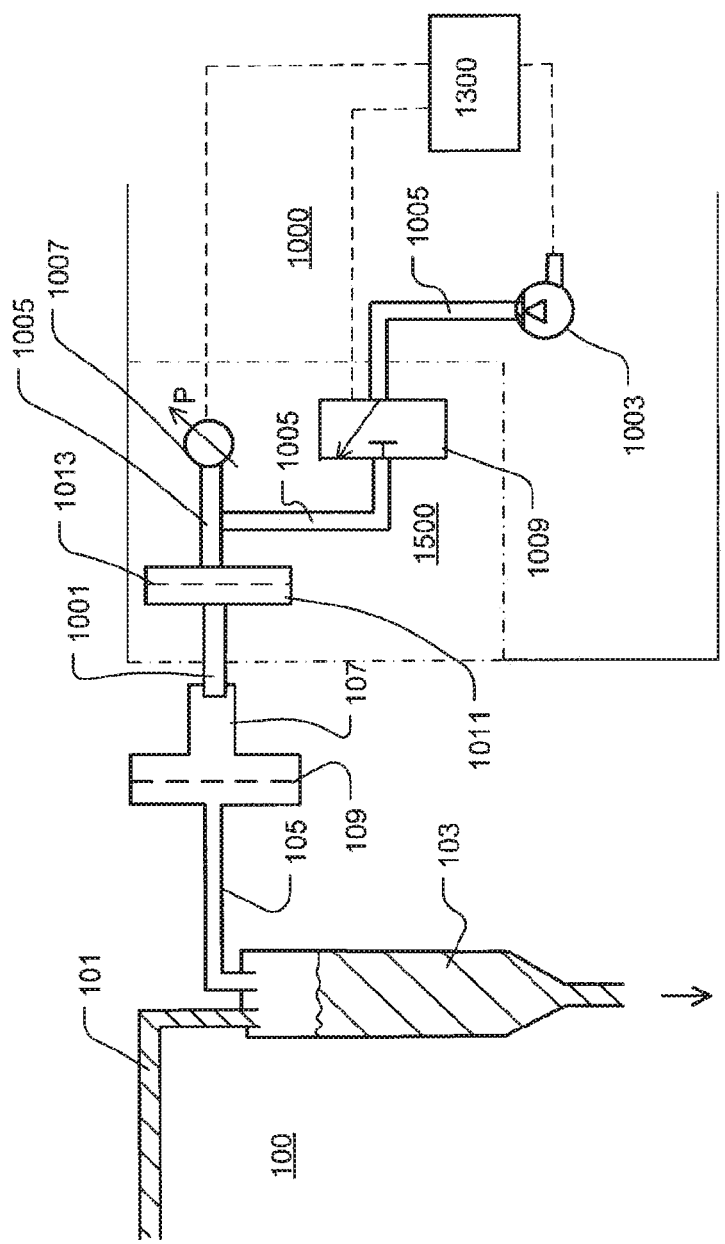
FIG. 1 shows a schematically simplified diagram of a blood treatment apparatus and a pressure measuring line of a blood tubing set.

FIG. 1 shows schematically very simplified sections of a blood treatment apparatus 1000 as well as sections of a blood tubing set 100.

The extracorporeal blood tubing set 100, which may optionally extend outside or inside a non-illustrated blood cassette, comprises a venous patient line 101 and optionally a venous bubble trap or catcher or a venous blood chamber 103. In use, the patient line 101 may be flown through in the direction of the indicated arrow towards the patient.

A pressure measuring line 105 is connected to the blood tubing set 100 (or to parts thereof). The pressure measuring line 105 starts, purely exemplarily, from the venous blood chamber 103. The pressure measuring line 105 may be the return pressure measuring line. It may be an open line.

The pressure measuring line 105 comprises a connector 107 which is provided and designed or embodied to connect the pressure measuring line 105 to a compressed air outlet 1001 of the blood treatment apparatus 1000. Purely optionally, the connector 107 and the compressed air outlet 1001 are female or male parts of a Luer connector, respectively, with a female or male sealing cone, respectively, or a corresponding Luer lock connector with additional security thread.

The compressed air outlet 1001 may be arranged in or on an exterior wall of the blood treatment apparatus 1000, e.g. in its housing wall.

The connector 107 of the pressure measuring line 105, or another section of the pressure measuring line 105, which during use of the pressure measuring line 105 is arranged in an area being flown through, or being flowable, by air, comprises an air-permeable membrane 109. The air-permeable membrane 109 is, purely exemplarily, embodied as hydrophobic air permeable membrane or hydrophobic filter.

The blood treatment apparatus 1000 comprises a compressor 1003 as one example of a compressed air device or compressed air source.

Compressor 1003 and compressed air outlet 1001 are connected in fluid communication via a compressed air line 1005. The compressor 1003 may optionally comprise further valves for a different or another use than that described herein.

A pressure sensor 1007 and an optional switch or change-over valve 1009 (alternatively or additionally a throttle, a switch, a lock and/or the like) are provided in or on the compressed air line 1005.

As can be seen in FIG. 1, the pressure sensor 1007 is integrated or contained in the compressed air line 1005 or is therewith in adequate or suitable fluid communication such that it can measure the pressure P in the pressure line 1005, which builds up due to operation of the compressor 1003, in case or when the switch valve 1009 (if present) is correspondingly switched and the compressor 1003 is activated, i.e. switched-on. The pressure sensor 1007 may be the return pressure sensor.

Purely exemplarily, the compressed air outlet 1005 passes or extends through an optionally provided protection filter 1011 which comprises a, preferably hydrophobic, permeable membrane 1013 in the flow path. If such air-permeable membrane 1013 is provided, the detection device 1300 may optionally be configured or programmed to correctively consider (e.g. by filtering, subtracting, etc.) the pressure resistance of the air-permeable membrane 1013 in the method.

The blood treatment apparatus 1000 comprises a detection device 1300. The latter is, as shown by dotted lines, connected in signal communication with the compressor 1003, with the pressure sensor 1007, and/or with the switch valve 1009, by way of example.

As shown by dot-dash lines, at least the compressed air outlet 1001 and the pressure sensor 1007, moreover optionally the switch valve 1009 and the protection filter 1011, if provided, may be part of the separate pressure measuring unit 1500 which is connected with the blood treatment apparatus 1000.

Figure 2:
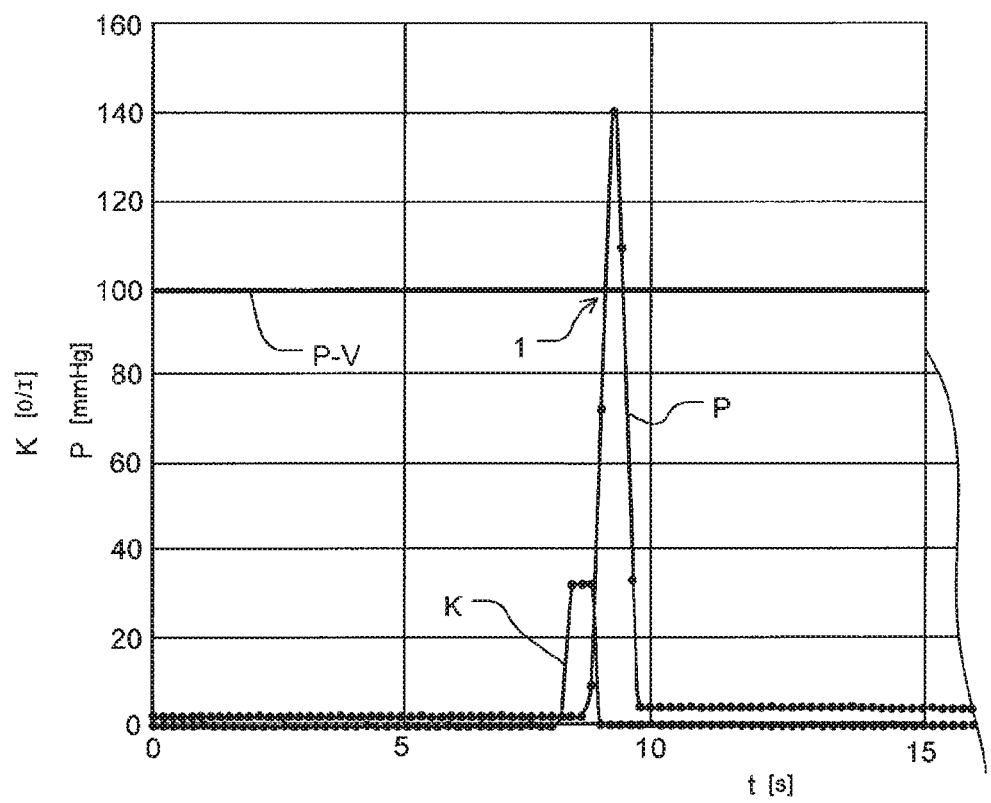
FIG. 2 shows a diagram in which the pressure over time, measured with the pressure sensor of FIG. 1, reveals a correct connection between the pressure measuring line and the compressed air outlet.

FIG. 2 shows a diagram in which the course of the pressure P (herein to be understood as first pressure (course) for differentiation) being measured by the pressure sensor 1007 of FIG. 1 is plotted in the unit mmHg, over the time t, in the unit s (seconds).

FIG. 2 further shows a second course K indicating the state of the compressor 1003 over time. The latter can be switched-on ("I") or supplying pressure or air flow, or it can be switched-off ("O") and not supplying neither pressure nor air flow.

It can be seen in FIG. 2 that the compressor 1003 begins to convey or supply air approximately at the time point "8.4 s". As a reaction hereunto, the air pressure increases in the compressed air line 1005 (see or compare to FIG. 1) as from approximately the time "8.8 s".

As it is further depicted in FIG. 2, the pressure P increases rapidly, and exceeds shortly after a threshold P-V. P-V is, in the example of FIG. 2, the threshold or criteria for the pressure from which on it is assumed that a correct connection between the pressure measuring line 105 and the compressed air outlet 1001 is achieved and thus assuring that a correct connection exists. The connection test executed is, therefore, considered successful.

The increase of P up to over or beyond P-V results from the configuration of the flow resistances of the connector 107 with the air-permeable membrane 109 and of the pressure measuring line 105. The flow resistance may be configured for example by selecting the air permeability of the membrane 109 (pore size, porosity, thickness of the air-permeable membrane), the free onflow surface of the air-permeable membrane 109, the interior geometry of the flown-through cross-sections of the connecter 107 and the diameter and length of the pressure measuring line 105.

FIG. 2 further shows that by exemplarily executing the method, as depicted in FIG. 2, the compressor 1003 is being switched-off already as soon as the measured pressure P has reached the threshold P-V. The further increase of the pressure P up to approximately 140 mmHg is no longer relevant in the example of FIG. 2; the method ends at the time when the increase in pressure to 100 mmHg (equals P-V) has been detected.

Due to the switching-off of the compressor 1003, the measured pressure P falls back to its initial value of 0 mmHg after completion of the method. The earliest possible switching-off of the compressor 1003, i.e. for example as soon as P is measured to have reached at least the value P-V, may serve for protecting the air-permeable membrane and be, therefore, advantageous.

As can also be seen in FIG. 2, there is no pressure-holding test. There is preferably no evaluation of the pressure P with respect to its decline. Preferably, no pressure value is integrated over time. Preferably, there is no evaluation of a release of the pressure measured by the compressor 1003.

Figure 3:
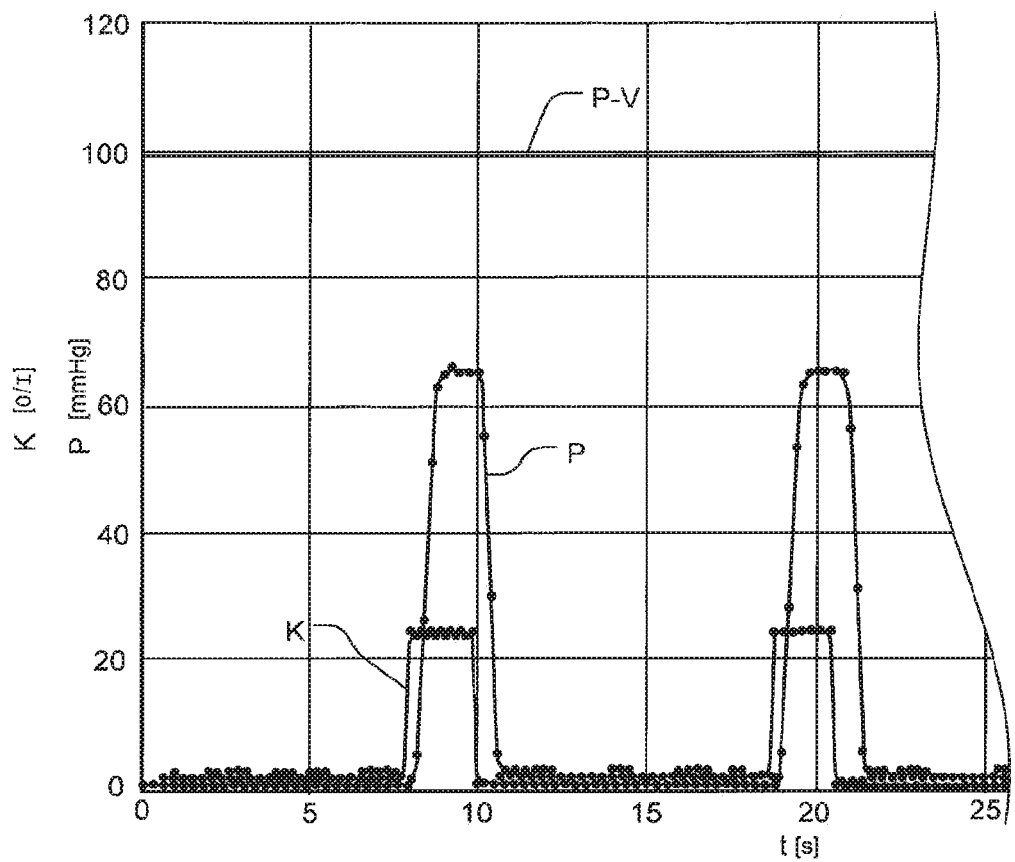
FIG. 3 shows a pressure course in the diagram known from FIG. 2 where the pressure measuring line is not connected to the compressed air outlet.

FIG. 3 shows in the diagram of FIG. 2 a course of pressure P, measured with the pressure sensor 1007, different from the one of FIG. 2. The course of pressure P shown in FIG. 3 however does not reach in its maximum of ca. 70 mmHg the threshold P-V. If this is still the case also after a preselected period of time, then the method is interrupted and repeated at about "18 s".

The course of pressure P shown in FIG. 3 does not reach the threshold P-V, because the air flow generated by the compressor 1003 encounters, comparatively only little resistance since the pressure measuring line 105 is not connected. Namely or indeed, the compressed air outlet 1001 (e.g. through their connector or Luer connector acting as throttle) and, if provided, also the device-sided air-permeable membrane 1013 act or effect as resistance or build up such resistance. This resistance is however less than in FIG. 2, where it is additionally effected by the connector 107 and by the air-permeable membrane 109.

The test executed by the method to indicate if a correct connection exists, is not passed: there is no connection.

Figure 4:
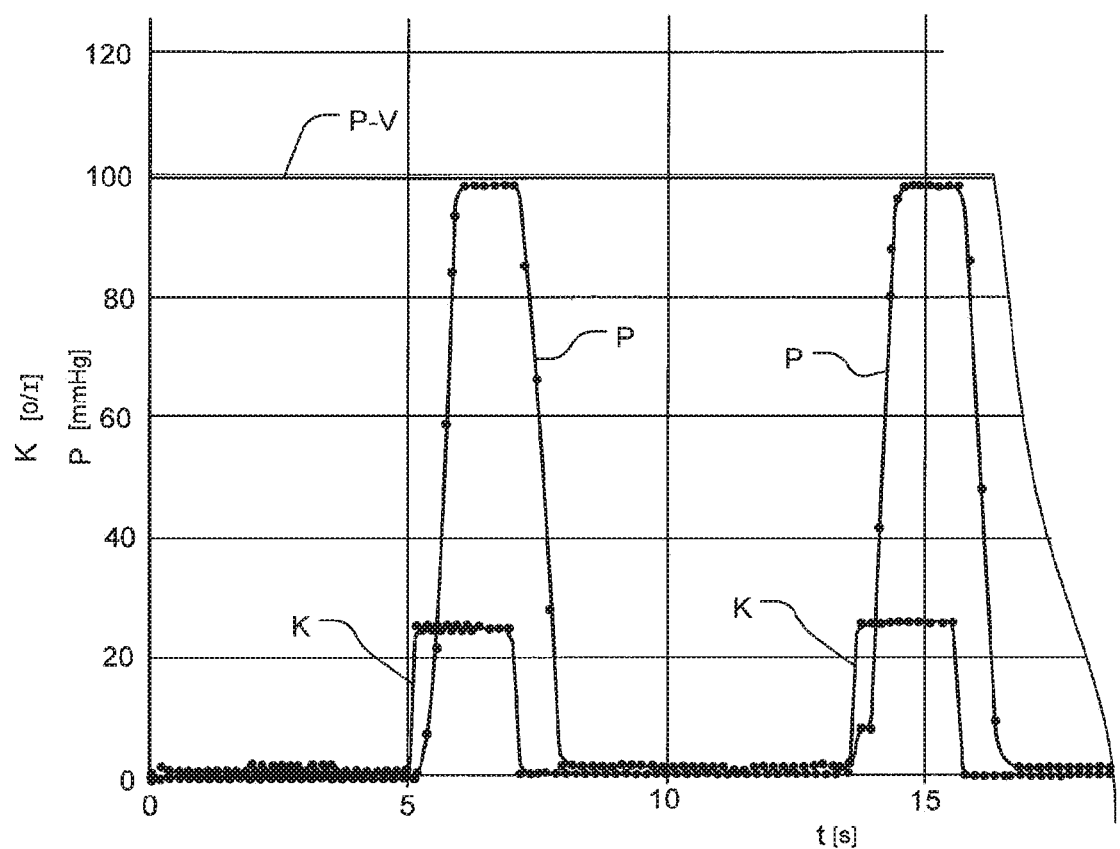
FIG. 4 shows a further pressure course in the diagram known from FIG. 2 in the case of an incorrect connection between the pressure measuring line and the compressed pressure outlet.

FIG. 4 shows in a diagram of FIG. 2 another course of pressure P measured by the pressure sensor 1007, different to the courses of FIG. 2 or of FIG. 3.

The pressure course P shown in FIG. 4 does not reach in its maximum of approximately 95 mmHg the threshold P-V. If this is still the case also after a preselected period of time, then the method is interrupted and repeated at about "14 s".

In contrast to FIG. 3, it is however seen with respect to the course of pressure P in FIG. 4 that not only the resistance of the connector 107 may be a cause, rather, there must be a further cause for the measured increase of pressure as a higher value P was measured in FIG. 4 than in for example FIG. 3. This further cause results from an existing connection between pressure measuring line 105 and compressed air outlet 1001, which however—one compares with the course of FIG. 2—must be faulty or incorrect or erroneous and that, for example, is based on or due to a defect air-permeable membrane 109, a defect pressure measuring line 105 or the use of a pressure measuring line 105 not authorized by the producer of the blood treatment apparatus for measuring pressure.

When passing and/or failing connection tests, corresponding messages may be output, as discussed supra.

In certain exemplary embodiments, the connector 107 with air-permeable membrane 109 and the pressure measuring line 105 are configured such that an additional loss or drop of pressure of 56 mmHg to 93 mmHg occurs if the elements are flown through with a standard flow of air (standard condition: 1 bar ambient pressure; 293.15 K ambient temperature) between 1.4 l/min and 2.1 l/min.

The length of the pressure measuring line (from the connector 107) to the bubble trap 103 is between 16.5 to 27.5 cm; preferably 22 cm; the outer diameter is 5.5 mm; the inner diameter is 3.5 mm; the material of the tube is preferably PVC (polyvinyl chloride). Preferably the pressure measuring line is permanently bonded to the connector 107 in a connecting piece or nozzle.

Preferably, the connector 107 of the free end is the female part of a Luer lock connector with female Luer cone and surrounding external thread.

The diameter of the smallest free flow cross section in the female Luer cone is preferably 2.5 mm; the material of the Luer cone is preferably PBT (polybutylene terephthalate).

The air-permeable membrane 109 in the connector 107 has preferably a free flow diameter of 10 to 14 mm, particularly preferred is 12 mm, being preferably perpendicular to the flow direction. The thickness of the air-permeable membrane 109 is preferably about 0.15 mm, by way of example.

The average pore diameter of the air-permeable membrane 109 (whose material may be, among others, PTFE (polytetrafluoroethylene)), is preferably between 0.1 μm and 0.6 μm, particularly preferred is 0.2 μm (micrometers).

The membrane is supported in the connector, preferably on both sides, optionally by radial supporting ribs in order to ensure the air permeability of the entire free cross section.

The connector 107 has preferably a color marking (it is, for example, at least partially made from blue resin or plastic) and the compressed air outlet 1001 has a corresponding marking (e.g. a blue color element), in order to additionally give the user a visual hint or clue for connecting or for the connection. This simplifies equipping the blood treatment apparatus 1000 with the blood tubing set 100, reduces the risk of errors occurring upon equipping and increases the safety of the patient.

The aforementioned figures or values correspond to those at which the applicant could particularly observe clear unambiguous results when executing the method. Therefore, they are advantageous and preferred.

The machine-side compressed air outlet 1001 may be a male part of the Luer lock connector with male Luer cone and surrounding internal thread. It can advantageously be made of stainless steel making it fully hygienic as it is easy to clean.

In certain embodiments and in particular with the aforementioned design of the connector 107 and air-permeable membrane 109, the duration of a successful measuring may last, in a correct connection state of the connector 107 at the compressed air outlet 1001, 1 to 2 s. A time-out may for example be set to less than or equal to 1 s. This allows a time-saving query or checking whether the connection is correct.

LIST OF REFERENCE NUMERALS 100 blood tubing set
101 venous patient line
103 bubble trap or venous blood chamber
105 pressure measuring line
107 connector
109 air-permeable membrane
1000 blood treatment apparatus
1001 compressed air outlet
1003 compressed air device, e.g. compressor
1005 compressed air line
1007 pressure sensor
1009 switch or changeover valve
1011 protection filter
1013 air-permeable membrane
1300 detection device
1500 pressure measuring unit
P measured pressure
K switch-on or activation condition of the compressor
P-V threshold for proper connection
t time

The invention claimed is:

1. A method for checking a connection between a compressed air outlet of a blood treatment apparatus and a pressure measuring line of an extracorporeal blood tubing set, the method comprising,
providing the blood treatment apparatus comprising:
a compressed air line;
a compressor in fluid communication with the compressed air line;
the compressed air outlet; wherein the compressed air outlet is in a constant open position such that the compressed air outlet is in fluid communication with both the compressed air line and an exterior of the blood treatment apparatus in fluid communication with both the compressed air line and an exterior of the blood treatment apparatus, wherein the compressed air outlet is connectable with a pressure measuring line; and
a pressure sensor arranged to measure a pressure prevailing at the compressed air outlet or in the compressed air line;
building up, using the compressor, pressure in the compressed air line and at the compressed air outlet;
measuring a pressure or a change of the pressure over time prevailing at the compressed air outlet or in the compressed air line using the pressure sensor;
evaluating an increase of the measured pressure or of the measured change of the pressure over time, by comparing the measured pressure or the measured change of the pressure over time with previously measured or stored values, thresholds, ranges, or courses; and
switching off the compressor when the measured pressure reaches a pressure threshold.

2. The method according to claim 1, wherein the evaluating the increase of the measured pressure or of the measured change of the pressure over time indicates whether the compressed air outlet and the pressure measuring line are connected.

3. The method according to claim 2, further comprising providing an assessment, including a list of minimum values, maximum values, patterns, curves, or courses of pressure increases or of pressure increases over time, which have been collected for or which designate, two or more preselected pressure measuring lines which differ from each other; and wherein the evaluating the increase of the measured pressure or of the measured change of the pressure over time comprises checking the list.

4. The method according to claim 3, wherein an indication of the assessment regarding the connection reveals that the connection does not exist or does not correctly exist or does not take place, if a preselected minimum increase in pressure or a preselected course of the increase in pressure is not reached or not detected by evaluating.

5. The method according to claim 4, wherein the indication of the assessment regarding the connection reveals that the connection does not exist or does not correctly exist, if the measured pressure increase does not reach or does not exceed a preselected pressure value.

6. The method according to claim 4, wherein the indication of the assessment regarding the connection reveals that the connection does not exist or does not correctly exist, if the measured pressure does not reach or exceed a preselected pressure value within a maximum period of time since the building up of the pressure.

7. The method according to claim 4, wherein when the indication of the assessment reveals that the connection does not exist or does not correctly exist, either: (i) an error message is issued or triggered, (ii) the method is cancelled or interrupted, or (iii) both.

8. The method according to claim 4, further comprising re-executing the method, if the indication of the assessment regarding the connection reveals that the connection does not exist or does not correctly exist, or in case a user requires or demands to do so.

9. The method according to claim 4, wherein when: (i) the indication of the assessment regarding the connection reveals that the connection does not exist or does not correctly exist or (ii) the increase of the measured change of the pressure over time is not included in the list, then the method further comprises disabling the beginning of or interrupting a blood treatment performed by the blood treatment apparatus.

10. The method according to claim 4, wherein when: (i) the indication of the assessment regarding the connection reveals that the connection does not exist or does not correctly exist or (ii) the increase of the measured change of the pressure over time is not included in the list, the method further comprises one or both of: (a) blocking treatment modalities of the blood treatment apparatus and (b) restricting treatment parameters of a blood treatment method performable or executable by the blood treatment apparatus.

11. The method according to claim 1, wherein the method is concluded prior to beginning a treatment of a patient using the extracorporeal blood tubing set.

12. The method according to claim 1, wherein the blood treatment apparatus is a device for apheresis, hemodialysis, hemofiltration, or hemodiafiltration.

13. A detection device configured for performing or prompting a method for checking a connection between a compressed air outlet of a blood treatment apparatus and a pressure measuring line of an extracorporeal blood tubing set, the method comprising:

providing the blood treatment apparatus comprising:
a compressed air line;
a compressor in fluid communication with the compressed air line;
the compressed air outlet; wherein the compressed air outlet is in a constant open position such that the compressed air outlet is in fluid communication with both the compressed air line and an exterior of the blood treatment apparatus, wherein the compressed air outlet is connectable with a pressure measuring line; and
a pressure sensor arranged to measure a pressure prevailing at the compressed air outlet or in the compressed air line;
building up, using the compressor, pressure in the compressed air line, and at the compressed air outlet;
measuring a pressure or a change of the pressure over time prevailing at the compressed air outlet or in the compressed air line using the pressure sensor;
evaluating an increase of the measured pressure or of the measured change of the pressure over time, by comparing the measured pressure or the measured change of the pressure over time with previously measured or stored values, thresholds, ranges, or courses; and
switching off the compressor when the measured pressure reaches a pressure threshold.

14. The detection device according to claim 13, comprising at least one display for displaying a result of the method.

15. The detection device according to claim 13, comprising at least one alarm device configured for issuing an alarm when the method reveals that the connection does not exist or does not correctly exist.

16. The detection device according to claim 13, wherein the detection device is configured to act on or to affect the blood treatment apparatus such that one or both of: (i) at least one treatment option, for which the blood treatment apparatus is designed, is not performable or executable, and (ii) a treatment is not performable by the blood treatment apparatus using preselected treatment parameters, when the method reveals that the connection does not exist or does not correctly exist.

17. The detection device according to claim 13, being or comprising either a control device, or a function test monitor, or both.

18. A blood treatment apparatus that is at least one of: (i) in signal communication with at least one detection device, (ii) connected to at least one detection device for signal communication, and (iii) comprising at least one detection device the at least one detection device configured for performing or prompting a method for checking a connection between a compressed air outlet of a blood treatment apparatus and a pressure measuring line of an extracorporeal blood tubing set, the method comprising:
providing the blood treatment apparatus comprising:
a compressed air line;
a compressor in fluid communication with the compressed air line;
the compressed air outlet; wherein the compressed air outlet is in a constant open position such that the compressed air outlet is in fluid communication with both the compressed air line and an exterior of the blood treatment apparatus, wherein the compressed air outlet is connectable with a pressure measuring line; and
a pressure sensor arranged to measure a pressure prevailing at the compressed air outlet or in the compressed air line;
building up, using the compressor, pressure in the compressed air line, and at the compressed air outlet;
measuring a pressure or a change of the pressure over time prevailing at the compressed air outlet or in the compressed air line using the pressure sensor;
evaluating an increase of the measured pressure or of the measured change of the pressure over time, by comparing the measured pressure or the measured change of the pressure over time with previously measured or stored values, thresholds, ranges, or courses; and
switching off the compressor when the measured pressure reaches a pressure threshold.

19. The blood treatment apparatus according to claim 18, wherein the blood treatment apparatus is a device for apheresis, hemodialysis, hemofiltration, or hemodiafiltration.

20. The blood treatment apparatus according to claim 18, further comprising the extracorporeal blood tubing set which is connectable with the blood treatment apparatus, wherein the extracorporeal blood tubing set comprises the pressure measuring line, a connector and at least one air-permeable membrane being arranged in the connector or at another point or site of the pressure measuring line.

21. A digital storage medium with electrically readable control signals that when executed by a hardware processor of a blood treatment apparatus cause the blood treatment apparatus to carry out operations comprising:
building up, using a compressor of the blood treatment apparatus, pressure in a compressed air line of the blood treatment apparatus, and at a compressed air outlet of the blood treatment apparatus; wherein the compressed air outlet is in a constant open position such that the compressed air outlet is in fluid communication with both the compressed air line and an exterior of the blood treatment apparatus;
measuring a pressure or a pressure over time prevailing at the compressed air outlet or in the compressed air line using a pressure sensor;
evaluating an increase of the measured pressure or of the measured pressure over time, by comparing the measured pressure or the measured change of the pressure over time with previously measured or stored values, thresholds, ranges, or course; and
switching off the compressor when the measured pressure reaches a pressure threshold.

* * * * *